United States Patent [19]
Mathes

[11] 3,973,566
[45] Aug. 10, 1976

[54] INHALATION DEVICE

[75] Inventor: Stanley Mathes, Mountain View, Calif.

[73] Assignee: Syntex Puerto Rico Inc., Humacao, P.R.

[22] Filed: Jan. 13, 1975

[21] Appl. No.: 540,613

[52] U.S. Cl. .............................. 128/266; 128/206; 128/208
[51] Int. Cl.² ........................................ A61M 13/00
[58] Field of Search ........... 128/205, 206, 208, 266; 222/193

[56] References Cited
UNITED STATES PATENTS

| | | | |
|---|---|---|---|
| 2,470,296 | 5/1949 | Fields | 128/206 |
| 2,503,732 | 4/1950 | Heisterkamp | 128/207 |
| 2,517,482 | 8/1950 | Hall | 128/208 X |
| 2,603,216 | 7/1952 | Taplin et al. | 128/206 |
| 2,672,865 | 3/1954 | Willis | 128/206 |
| 3,807,400 | 4/1974 | Cocozza | 128/266 |
| 3,858,583 | 1/1975 | Hallworth | 128/266 |

FOREIGN PATENTS OR APPLICATIONS

| | | | |
|---|---|---|---|
| 1,331,216 | 9/1973 | United Kingdom | 128/266 |
| 1,118,341 | 7/1968 | United Kingdom | 128/266 |

*Primary Examiner*—Aldrich F. Medbery
*Attorney, Agent, or Firm*—Joseph I. Hirsch; William B. Walker

[57] ABSTRACT

An inhalation device having an elongate housing having an emptying chamber adjacent that end of housing which is adapted for insertion into the mouth or nose of a user. A plurality of passageways extending essentially perpendicular to the longitudinal axis of the housing intersect with the inner end of the emptying chamber. Adjacent that end of the emptying chamber closest to the passageways, the housing has means for receiving or presenting a unit dose of powdered medicament for administration. During inhalation, the powdered medicament is entrained in the air stream being inhaled and is carried into the nose, throat or lungs of the user where beneficial or therapeutic action of the medicament occurs.

18 Claims, 2 Drawing Figures

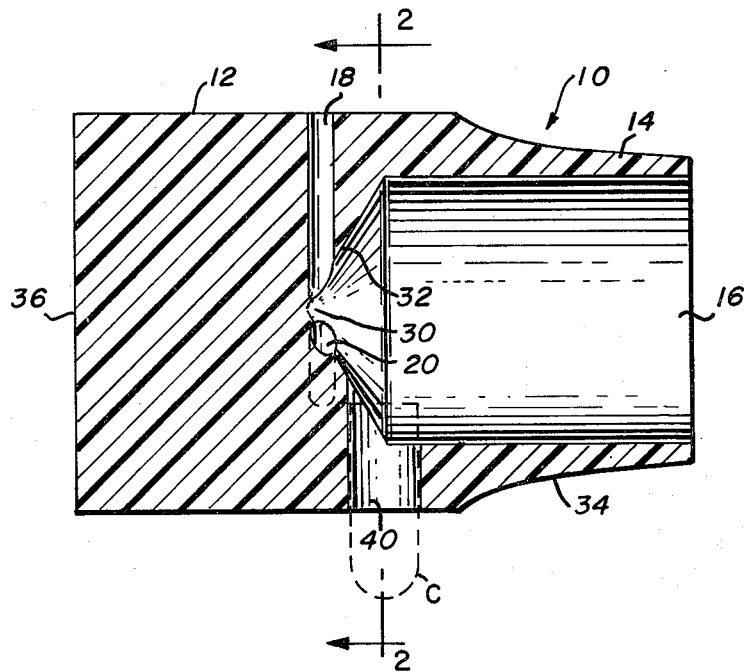
Fig_1
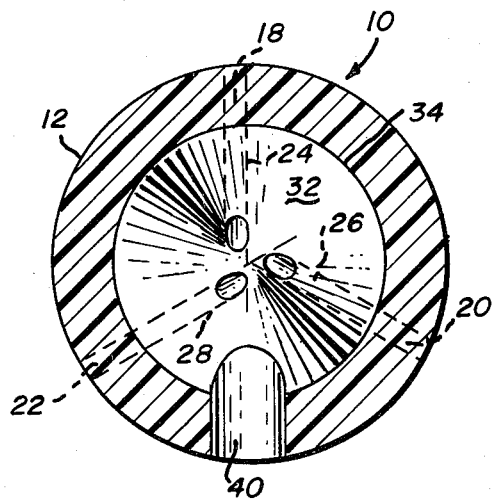
Fig_2

INHALATION DEVICE

FIELD OF THE INVENTION

This invention is related to devices for the administration of powdered medicaments by inhalation. More particularly, this invention relates to an inhalation device having, in the essential aspects thereof, no moving parts, yet which is capable of causing a powdered medicament, held within a container inserted into, or adjacent, the device, to be rapidly and effectively dispensed from the container, entrained in the air stream being inhaled and, thusly, carried into the nose, throat or lungs of the user where beneficial action of the medicament occurs.

BACKGROUND OF THE INVENTION

Known, prior art inhalation devices include, for example, those shown in U.S. Pat. Nos. 988,352; 2,507,702; and 2,603,216; and Great Britain Pat. No. 1,118,431.

SUMMARY OF THE INVENTION

The inhalation devices of the present invention include an elongate housing having an emptying chamber adjacent that end of the housing which is adapted for insertion into the mouth or nose of the user. A plurality of passageways extending essentially perpendicular to the longitudinal axis of the housing intersect with the inner end of the emptying chamber. The intersection of the longitudinal axes of the passageway are off-set with respect to the longitudinal axis of the emptying chamber such that, upon inhalation, a turbulent flow of air is generated within, and through, the emptying chamber. Means are provided adjacent the intersection of the passageways with the emptying chamber for receiving or presenting a unit dose of powdered medicament for administration. As shown, the housing has an opening or port adapted to receive and hold a powdered medicament-holding container from which the medicament is to be entrained in the air stream passing through the device during inhalation. During inhalation, the air stream swirling through the emptying chamber causes the powdered medicament to be expelled from the container, and entrained in the air stream being inhaled and carried into the nose, throat or lungs of the user where beneficial or therapeutic action of the medicament occurs.

Container, as used herein, is intended to include any means by which a unit dose of medicament is presented to the device for administration. Capsules are the presently preferred form of containers; however, it is contemplated that other forms would be equally suitable if appropriate structural modifications of the device, to accommodate the different carrier, are made as, and if, necessary.

The container, in one aspect of the present invention, is manually opened, just prior to insertion into the device, to expose the medicament as is necessary for entrainment during inhalation. Optionally, in another aspect of this portion of the invention, the device can have conventional means associated therewith for opening the container after it has been inserted into the device or for automatically opening the container as it is being inserted into the device. In either case, such means eliminate the need to manually open the container prior to insertion and, thusly, reduce the possibility of inadvertent spillage of the medicament prior to inhalation.

It has been found that, with the inhalation devices of this invention, the powdered medicament held within the container is rapidly and efficiently entrained in the air stream passing through the device during inhalation, and, as such, is carried into the nose, throat or lungs of the user for beneficial action of the medicament to occur.

BRIEF DESCRIPTION OF THE DRAWINGS

The foregoing and still further features and advantages of the present invention will become more apparent from the following detailed description, taken together with the accompanying drawings therein:

FIG. 1 is a vertical cross-sectional view of the inhalation device of the present invention; and FIG. 2 is a cross-sectional view of the inhalation device of FIG. 1 taken along line 2—2 of FIG. 1.

In the discussion below, reference will be made to a capsule as the exemplary container for presenting the medicament to the device for administration. As set forth above, other containers are contemplated for use with the device described herein.

Referring to FIG. 1 there is shown an inhalation device 10 having a substantially cylindrical elongate housing 12 (as can best be seen FIG. 2). At one end of housing 12 is a mouthpiece 14 intended for insertion into the mouth of the user thereof. Mouthpiece 14 can be redesigned to permit insertion into the nasal passages or, if desired, an adaptor (not shown) can be placed over the mouthpiece to permit nasal use. Adjacent mouthpiece 14 is an emptying chamber 16 connected at the inner end thereof to passageways 18, 20 and 22 extending perpendicularly, or essentially perpendicularly, to the longitudinal axis of device 10. As can best be seen in FIG. 2, the longitudinal axes of cylindrical passageways 18, 20 and 22 are off-set with respect to the longitudinal axis of cylindrical emptying chamber 16. In particular, as shown in FIG. 2, the extensions of the left-hand edges 24, 26 and 28 respectively, intersect along the longitudinal axis of emptying chamber 16. This intersection also forms the apex 30 of cone-shaped surface 32 connecting the apex with the inner cylindrical surface 34 of emptying chamber 16. By off-setting the axes of the passageways in this manner, turbulent air flow is created in emptying chamber 16 during inhalation, a component of which is directed into or enters opening or port 40 adjacent the lower, inner end of chamber 16. Prior to inhalation, an opened capsule C, as shown in dotted outline in FIG. 1, is inserted into port 40 where it is held in place during inhalation. It is contemplated that passageways 18, 20 and 22 can be angled slightly toward end 36 of the inhalation device. In addition, the container port can be tilted (up to about 40°) toward the passageways (i.e., away from the output end of the housing) to further assist in causing the powdered medicament to be expelled from the container, for example as shown in copending application Ser. No. 540,632, filed Jan. 13, 1975. During inhalation, air drawn through passageways 18, 20 and 22 and emptying chamber 16, causes the powdered medicament to be expelled from the capsule, entrained in the air flowing through the device and carried into the nose, throat or lungs of the user where beneficial action of the medicament occurs.

In use, the patient manually opens the medicament-holding capsule or other medicament-holding container, and inserts the half-open medicament-holding portion thereof into port 40 essentially to the position shown in dotted outline in FIG. 1. The mouthpiece is then taken into the mouth and, upon inhalation, the air flowing through the device causes the medicament in the capsule to be entrained in the air stream flowing through emptying chamber 16.

As set forth above, means can be provided to open the medicament-holding carrier after it has been inserted into the device or to automatically open the container upon insertion thereof into port 40. For example, a slide having a sharp cutting edge can be manually pushed against the top of the medicament-holding carrier, while held within the device, to slice open the top thereof and thereby expose the medicament to be administered. Or the capsule, as it is being inserted, can be made to contact a sharp edge which will cut off the top of the capsule and, as with the prior means, expose the contents thereof. These opening mechanisms are shown, for example, in copending application Serial No. 633,780, filed Nov. 20, 1975. In either case, these means, and other means equivalent thereto, eliminate the need to manually open the container prior to insertion thereof into the inhalation device. This, in turn, reduces the possibility for spillage of the medicament prior to inhalation.

The entire device can be made of metal but preferably is made of suitable plastic material, such as nylon, polyacetal or polypropylene. With the exception of the capsule or other medicament-holding container, the device, in its basic elements, is preferably of unitary construction, although multi-piece construction is contemplated, especially where means are provided to open the medicament-holding container. The device of this invention can be manufactured quite readily, thereby effecting substantial cost reduction in the manufacturing process, without adversely affecting medicament administration during inhalation.

The physical properties (i.e., flow characteristics) of each powdered formulation will affect the ease or manner in which it is dispensed with these or other inhalation devices. However, for a given powdered formulation varying the diameter of the passageways, the positioning of port 40 (from the position as shown toward the output end of chamber 16), the angle tilt of port 40, the distance between the level of the powdered medicament in the container and the inside surface of the emptying chamber, and/or, in general, the overall configuration and shape of chamber 16 and passageways 18, 20 and 22, the device of this invention can be designed to deliver the medicament in a different number of inhalations or in a longer or shorter period of time, depending upon the nasal or lung capacities of each particular user. Quite obviously, no single device will be suitable for all persons requiring administration of powdered medicaments since, for example, people with differing lung capacities are known to generate flow rates of 30 liters/minute or so to about 120 liters/minute or so through inhalation devices of this and known types. Nonetheless, the device of this invention affords such variability, through proper selection of the various design parameters, that a device, embraced within the scope of this invention, can be designed for a particular patient-generated flow rate to deliver the medicament according to a certain set of pre-determined objectives (for example, slow or fast administration, one or more inhalations, etc.). The net result is that a family of devices, all embraced within the present invention, can be designed, each of which will deliver the medicament under a given set of selected administration conditions. Conversely, the devices of this invention can be designed to cover an extensive range of operating conditions and thus be suitable for use by a variety of persons having differing inhalation abilities or capacities.

While the present invention has been described with reference to specific embodiments thereof, it will be understood by those skilled in this art that various changes may be made and equivalents may be substituted without departing from the true spirit and scope of the invention. Additionally, other modifications may be made to adapt a particular situation, material or composition of matter, structural desirability, or then-present objective to the spirit of this invention without departing from its essential teachings.

What is claimed is:

1. An inhalation device comprising an elongate housing having an emptying chamber adjacent the output end of said housing, said emptying chamber terminating, at the inner end thereof, in an inner surface; a plurality of passageways extending substantially perpendicular to the longitudinal axis of said housing and intersecting with said inner end of said emptying chamber, the longitudinal axes of said passageways intersecting adjacent said inner end, the intersection of the longitudinal axes of said passageways being off-set with respect to the longitudinal axis of said emptying chamber; and means adjacent the inner end of said emptying chamber for receiving a medicament-holding container, said container receiving means comprising an exterior opening in said housing into which the container can be directly inserted from the exterior of said device, whereby during inhalation, turbulent air flow is generated within, and through, said emptying chamber, a component of which flows into said opening whereby medicament held in a medicament-holding container positioned in said opening is dispensed therefrom.

2. The device of claim 1 wherein said emptying chamber is substantially cylindrical and terminates, at said inner end thereof, in a substantially cone-shaped surface, said passageways intersecting with said emptying chamber along said cone-shaped surface.

3. The device of claim 2 wherein there are three passageways spaced about 120° from each other, said passageways being perpendicular to the longitudinal axis of said housing.

4. The device of claim 1 wherein there are three passageways spaced about 120° from each other.

5. The device of claim 1 wherein said opening in said housing is adjacent the interface between said emptying chamber and said passageways.

6. The device of claim 1 wherein the longitudinal axis of said opening is tilted toward said inner end of said emptying chamber at an angle up to about 40° from the vertical 7. An inhalation device comprising an elongate housing having an emptying chamber adjacent the output end of said housing, said emptying chamber being substantially cylindrical and terminating, at the inner end thereof, in a substantially cone-shaped surface; a plurality of passageways extending substantially perpendicular to the longitudinal axis of said housing and intersecting with the inner end of said emptying chamber along said cone-shaped surface, the intersection of the longitudinal axes of said passageways being off-set with respect to the longitudinal axis of said emptying chamber; an exterior opening in said housing adjacent the interface between said emptying chamber and said passageways for receiving a medicament-holding container directly from the exterior of said device, whereby, during inhalation, turbulent air flow is generated within, and through, said emptying chamber, a component of which flows into said opening whereby the medicament held in the medicament-holding container is dispensed therefrom.

8. The device of claim 7 where there are three passageways spaced about 120° from each other.

9. The device of claim 1 wherein said passageways intersect with said emptying chamber along said inner surface.

10. The device of claim 9 wherein there are three passageways spaced about 120° from each other, said passageways being perpendicular to the longitudinal axis of said housing.

11. The device of claim 1 wherein said container receiving means is adapted to hold in place a medicament-holding container.

12. The device of claim 1 wherein the combined cross-sectional area of said passageways is less then the cross-sectional area of said emptying chamber.

13. An inhalation device comprising an elongate housing having an exterior emptying chamber adjacent the output end of said housing, said emptying chamber being substantially cylindrical and terminating, at the inner end thereof, in a substantially cone-shaped surface; a plurality of passageways extending substantially perpendicular to the longitudinal axis of said housing and intersecting with the inner of said emptying chamber along said cone-shaped surface, the intersection of the longitudinal axes of said passageways being off-set with respect to the longitudinal axis of said emptying chamber, the cross-sectional area of said passageways being less than the cross-sectional area of said emptying chamber; an opening in said housing adjacent the interface between said emptying chamber and said passageways for receiving a medicament-holding container directly from the exterior of said device, said opening being adapted to securely hold a medicament-holding container so as to prevent movement thereof during inhalation, whereby, during inhalation, turbulent air flow is generated within, and through, said emptying chamber, a component of which flows into said opening whereby medicament held in a medicament-holding container positioned in said opening is dispensed therefrom.

14. The device of claim 13 where there are three passageways spaced about 120° from each other.

15. The device of claim 13 wherein the longitudinal axis of said opening is tilted toward said inner end of said emptying chamber at an angle up to about 40° from the vertical.

16. The device of claim 13 wherein the extensions of either the right-hand or left-hand edges of said passageways form a common intersection with the apex of said emptying chamber along the longitudinal axis of said emptying chamber.

17. The device of claim 1 wherein the extensions of either the right-hand or left-hand edges of said passageways form a common intersection.

18. The device of claim 16 wherein said intersection is along the longitudinal axis of said emptying chamber.

* * * * *

UNITED STATES PATENT AND TRADEMARK OFFICE
CERTIFICATE OF CORRECTION

PATENT NO. : 3,973,566

DATED : August 10, 1976

INVENTOR(S) : STANLEY MATHES

It is certified that error appears in the above–identified patent and that said Letters Patent are hereby corrected as shown below:

Claim 13, line 14, after "an" insert -- exterior --.

Signed and Sealed this

Nineteenth Day of October 1976

[SEAL]

Attest:

RUTH C. MASON
Attesting Officer

C. MARSHALL DANN
Commissioner of Patents and Trademarks